(12) United States Patent
Schmoll et al.

(10) Patent No.: US 10,026,504 B2
(45) Date of Patent: Jul. 17, 2018

(54) SYSTEM AND METHOD FOR CONTROLLING A DATA TRANSMISSION TO AND/OR FROM A PLURALITY OF MEDICAL DEVICES

(75) Inventors: Horst Schmoll, Guxhagen (DE); Matthias Paetzold, Melsungen (DE)

(73) Assignee: B. BRAUN MELSUNGEN AG, Melsungen (DE)

( * ) Notice: Subject to any disclaimer, the term of this patent is extended or adjusted under 35 U.S.C. 154(b) by 1213 days.

(21) Appl. No.: 13/574,206

(22) PCT Filed: Feb. 24, 2011

(86) PCT No.: PCT/EP2011/052728
§ 371 (c)(1),
(2), (4) Date: Oct. 10, 2012

(87) PCT Pub. No.: WO2011/104296
PCT Pub. Date: Sep. 1, 2011

(65) Prior Publication Data
US 2013/0030830 A1 Jan. 31, 2013

(30) Foreign Application Priority Data
Feb. 26, 2010 (DE) .................. 10 2010 009 540

(51) Int. Cl.
G16H 10/60 (2018.01)
G06Q 50/22 (2018.01)
(Continued)

(52) U.S. Cl.
CPC ............ *G16H 10/60* (2018.01); *G06Q 50/22* (2013.01); *G16H 40/20* (2018.01); *G16H 80/00* (2018.01)

(58) Field of Classification Search
CPC ........ G06Q 50/22; G06Q 50/24; G06Q 10/10; G06Q 10/00; G06Q 10/20; G06F 19/3468;
(Continued)

(56) References Cited

U.S. PATENT DOCUMENTS

2003/0067892 A1 4/2003 Beyer et al.
2004/0143677 A1 7/2004 Novak
(Continued)

FOREIGN PATENT DOCUMENTS

EP 1 515 496 A2 3/2005
JP A S63-10269 1/1988
(Continued)

OTHER PUBLICATIONS

Intellectual Property of Singapore Written Opinion dated Jan. 14, 2013.
(Continued)

Primary Examiner — Maroun P Kanaan
(74) Attorney, Agent, or Firm — RatnerPrestia

(57) ABSTRACT

The invention relates to a system for controlling a data transmission to and/or from a plurality of medical devices, said plurality of medical devices being divided into individual groups, each of which comprises at least one medical device. Each group of medical devices on a first data transmission level is directly connected via a respective first network to a communication device for transmitting, storing, and controlling data, said communication device being on a second transmission level, and a plurality of said communication devices exchange data with a common central server device for storing, controlling, and data transmission, said server device being on a third data transmission level.

18 Claims, 3 Drawing Sheets

Figure 1:
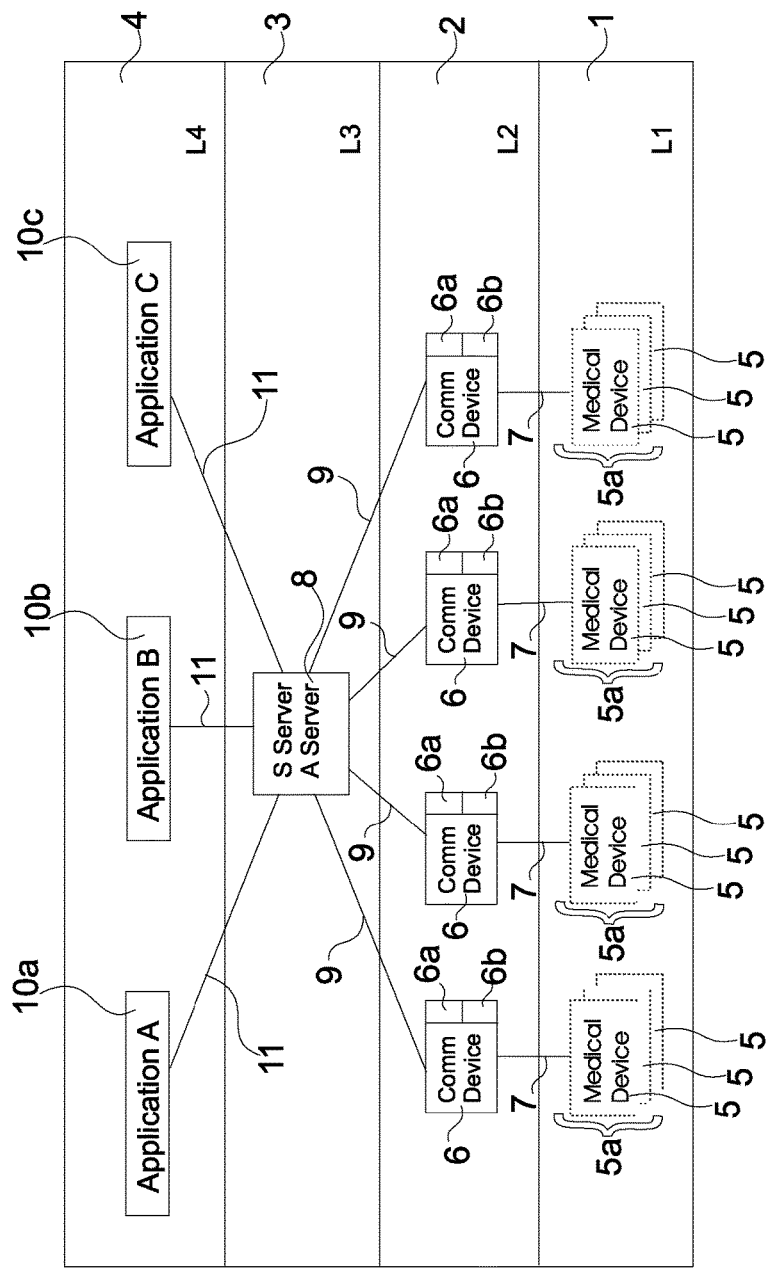

(51) Int. Cl.
*G16H 80/00* (2018.01)
*G16H 40/20* (2018.01)

(58) Field of Classification Search
CPC .. G06F 19/327; G06F 19/322; G06F 19/3406;
G06F 8/65; G06F 19/345; G06F 11/1464;
G06F 17/30864; G06F 19/30; G06F
19/3418; G16H 10/00; G16H 10/20;
G16H 10/40; G16H 10/60; G16H 10/65;
G16H 15/00; G16H 20/00; G16H 20/10;
G16H 20/13; G16H 20/17; G16H 20/30;
G16H 20/40; G16H 20/60; G16H 20/70;
G16H 20/90; G16H 30/00; G16H 40/00;
G16H 40/20; G16H 40/40; G16H 40/60;
G16H 40/63; G16H 40/67; G16H 50/00;
G16H 70/00; G16H 70/20; G16H 70/40;
G16H 70/60
USPC ......................................................... 705/2, 3
See application file for complete search history.

(56) References Cited

U.S. PATENT DOCUMENTS

| | | | |
|---|---|---|---|
| 2005/0038674 A1* | 2/2005 | Braig et al. | 705/2 |
| 2006/0031378 A1 | 2/2006 | Vallapureddy et al. | |
| 2009/0058635 A1 | 3/2009 | LaLonde et al. | |
| 2009/0157695 A1* | 6/2009 | Roberts | 707/10 |
| 2009/0198307 A1 | 8/2009 | Mi et al. | |
| 2009/0238087 A1 | 9/2009 | Shikowitz et al. | |

FOREIGN PATENT DOCUMENTS

| | | |
|---|---|---|
| JP | A 2008-508029 | 3/2008 |
| JP | A 2009-522060 | 6/2009 |
| JP | A 2009-525822 | 7/2009 |
| JP | A 2010-502291 | 1/2010 |
| RU | 2273964 | 3/2005 |
| RU | 2292646 | 1/2007 |
| WO | WO 2006/020212 | 2/2006 |
| WO | WO 2006/067271 A1 | 6/2006 |
| WO | WO 2007/081829 | 7/2007 |
| WO | WO 2007/095093 | 8/2007 |
| WO | WO 2008/030495 | 3/2008 |

OTHER PUBLICATIONS

Memo including English translation of Mexican examination report for MX/a/2012/008432 dated Oct. 8, 2013.
English summary of an examination report issued for Mexican Patent Application No. MX/a/2012/008432.
Examination Report for Australian Patent Application No. AU 2011219809 dated May 30, 2013.
International Search Report for PCT/EP2011/052728, dated Aug. 5, 2011.
Japanese Office Action with translation for U.S. Appl. No. 13/574,206 parallel application dated Dec. 25, 2013.
International Preliminary Report on Patentability for PCT/EP2011/052728, dated Oct. 4, 2012.
Russian Decision on Grant (translation) for RU 2012129949/08(047043) dated Nov. 14, 2014.
Russian Office Action with translation for RU 2012129949/08(047043) dated Apr. 2, 2014.
Mamkin, V.R., et al., "Can bus gateway for data acquisition and control," Sep. 10, 2006, p. 208, Proceedings of RuPAC, Novosibirsk, Russia, XP055340665, Found in the Internet: URL:https://accelconf.web.cern.ch/accelconf/r06/PAPERS/MODP01.PDF [Found on Jan. 31, 2017], 1 pg.
European Summons for European Application No. 11705556.6, dated Feb. 16, 2017, including machine translation, 10 pages.
Canadian Examination Report for CA 2,786,823 dated May 4, 2015.

* cited by examiner

SYSTEM AND METHOD FOR CONTROLLING A DATA TRANSMISSION TO AND/OR FROM A PLURALITY OF MEDICAL DEVICES

CROSS-REFERENCE TO RELATED APPLICATIONS

This application is a U.S. National Stage Application under 35 U.S.C. § 371 of International Application No. PCT/EP2011/052728, filed Feb. 24, 2011, which claims the benefit of German Application No. 10 201 0 009 540.0, filed Feb. 26, 2010.

DESCRIPTION

The invention relates to a system and a method of controlling a transmission of data to and/or from a plurality of medical appliances according to the preambles of claims 1 and 9.

In clinics and hospitals, networks for the transmission of data are frequently made available, which are provided in order to make available data communication with a plurality of medical appliances on the one hand and a server or a server device on the other hand. Networks of this type have the task of data transmissions taking place in near real time. This applies both to data which are produced at the medical appliances which are frequently connected to patients who occupy a hospital bed and which have to be sent to the central server device in order to monitor, evaluate and display the data, and to data which are to be sent from the server device centrally to the various medical appliances. This data transmission has to be carried out in near real time and in a trouble-free manner, which is frequently not possible just as all the medical appliances access a common network and overloading of the network frequently occurs as a result of this.

In addition, an overloading of this type can lead to an interruption in the data transmission and, in this way, a trouble-free data transfer cannot be carried out. This frequently results in large intermediate memories being provided in the medical appliances in order to store the data—which are currently being produced in the medical appliance or have been received beforehand—temporarily in the event of failure or overloading of the network.

Reading out this intermediate memory is made possible again only if a fixed data transmission connection to the server device has been set up, for example after the reduction of an overloading of the network.

Consequently, the object of the present invention is to make available a system and a method of controlling a transmission of data to and/or from a plurality of medical appliances, which will provide a trouble-free continuous transmission of data between the medical appliances on the one hand and a server device on the other hand, without a loss of data during near real time transmission of the data and an overloading of a network taking place.

This object is attained with respect to the system by the features of claim 1 and with respect to the method by the features of claim 9.

An essential aspect of the invention lies in the fact that in the case of a system for controlling a transmission of data to and/or from a plurality of medical appliances, the plurality of medical appliances being subdivided into individual groups with at least one medical appliance in each case, each group of medical appliances on a first data transmission stage is directly connected by way of a first network in each case to a communication device arranged on a second data transmission stage for the transmission, storage and control of data, and means are provided which are designed in order that a plurality of these communication devices on a third data transmission may exchange data with a common central server device arranged on a third data transmission stage for the storage, control and transmission of data. Means of this type can be a second network which connects the communication device directly to the server device. Alternatively or in addition, means of this type can constitute external storage media, such as for example USB sticks or memory cards which can be used for the transmission of data.

By means of a system of this type for controlling a transmission of data it is advantageously made possible that on account of the multiple-stage arrangement of the individual system components involved in the transmission of data not only the overloading of the network with data is minimized and thus an overloading of the networks involved is prevented, but a trouble-free transmission of data between the medical appliances on the one hand and the server device on the other hand is also ensured. This is because on account of the connection of the individual medical appliances, which are divided into groups, to one communication device in each case, which is otherwise designed in such a way that it can communicate in an autarkical manner, i.e. independently of the server device, with the medical appliances, which are preferably infusion pumps, and can also store data, a direct connection between a communication device in each case on the one hand and a medical appliance on the other hand is formed as an exclusive connection of the first network.

This has the result that when using a network of the CAN type for example no overlapping of data or data packets in terms of time or quantities can occur between medical appliances and a centrally arranged server device, since the exclusive direct line between the communication device and one of the medical appliances reduces and almost eliminates the latency times and data losses in the transmission of data. As a result of this, not only repetition loops, which frequently have to take place for a successful transmission of data by way of a network which is to ensure the supply of a plurality of medical appliances at the same time, but also update terminations during the updating of the software of the medical appliances are prevented.

In addition, on account of this direct line between the communication device and the medical appliances a trouble-free transmission of data from the medical appliance to the communication device or vice versa can take place. This can relate to both appliance-specific and patient-specific data on patients who are connected up to the medical appliances, such as insulin pumps, and medicine-specific data which are to be transmitted from the server device to the medical appliances.

To this end the central server device has an application server unit and a memory unit, the application server unit being connected to application operation units on a fourth data transmission stage by means of a third network. In this way, a plurality of application operation units are arranged on a further data transmission stage of this communication structure built up in the form of a cascade or a multiplicity of stages, as a result of which a plurality of devices, units and medical appliances loosely communicating with one another are formed on various stages of this communication structure and they can function and act relatively independently in order to continue to maintain the communication with the adjacent devices/units/medical appliances of the next lower or the next higher stage. This makes possible a reduction in the susceptibility to communication failures, such as can frequently occur for example in the use of wireless LAN (WLAN) with a server which is directly connected to the medical appliances in the entire clinic by way of a network of this type.

Each communication device is provided for this purpose with at least one first memory unit and one first control unit in order to store temporarily data arriving and received from the medical appliances of the group, in particular appliance-specific and patient-specific data on patients who are connected up to the medical appliances, and to pass them on in a bundled manner to the memory server unit.

In the same way, the first memory unit and the first control unit of each communication device are suitable for storing temporarily data arriving and received from the memory server unit or application server unit, in particular medicine-specific data, and to pass them on to selected medical appliances upon demand or if required. This makes it possible for data to be capable of being sent both from the communication device to the medical appliances and from the medical appliances to the communication device, in which case all the data can be temporarily stored inside each communication device and can optionally also be read directly out of or written into this communication device without the aid of a server device. As a result, a virtually independent first network is possible between a group of medical appliances on the one hand and at least one communication device on the other hand.

In the same way, the second network which is built up between a plurality of communication devices of this type on the one hand and the server device on the other hand, should be regarded as being a network system independent of the other networks. In this respect a transmission of data from the server device to the individual communication devices, which is necessary for example in order to pass on data on medicines which are available in a new form by way of the server device, to the individual communication devices and thus to the medical appliances, can take place first by means of the second network, and these data can be stored temporarily inside the individual communication devices in order to be subsequently passed on to the medical appliances if required and in a suitable operating state of the aforesaid medical appliances. This can be present for example if the medical appliance designed in the form of an insulin pump is not carrying out any administration of medicine in the form of insulin to the patient.

In addition, the third network between the server device and the application operation units, which can be arranged at a distance from the server device, is to be regarded as being autarkic. This independent third network can connect the application operation units to the application server unit by means of a web interface and a web browser for example and can thus permit the operation, control, uploading and reading out of the data stored on the server device.

The data which are stored on the server device and which are preferably stored in the memory server unit can likewise be displayed visually, it being possible for this display to take place both on the server device and in one or more application operation units which are arranged at a distance from the server device.

A method according to the invention for controlling the transmission of data to and/or from the plurality of medical appliances is characterized in that each group of medical appliances on a first data transmission stage transmits data from or to a communication device arranged on a second data transmission stage by way of a first network in each case and stores them at the receiver location or at the transmission location and optionally uses them to control the appliance or the device respectively. These can be appliance-specific configuration data, appliance-specific medicine data, appliance-specific software programs as well as the collection and evaluation of appliance-specific status information and the collection and evaluation of appliance-specific therapy information.

The appliances, which operate on the first data transmission stage and which otherwise operate likewise virtually independently of the power supply and thus function in an autarkic manner, are thus controlled by the communication devices by way of configuration files and commands and pass on operating, status and medical data to the communication device the other way round.

The communication devices on the second data transmission stage are likewise designed to operate virtually independently of the network and, in particular, in a manner autarkic of the server device, and they receive configuration files and commands from the server device on occasion in order to pass these on to the medical appliances attached to the respective communication device.

Operating, status and medical data of all the attached medical appliances are likewise received and temporarily stored the other way round in order to then pass them on bundled or concentrated to the server device on the third data transmission stage.

In addition, the time-wise and functional behaviour of the communication devices is preferably controlled by way of the central server device on the third data transmission stage by the transmission of control data of this type.

The server device arranged on the third data transmission stage is preferably arranged centrally inside the clinic and is controlled by the application operation units on the fourth data transmission stage. A control of this type can cause the appliance-specific configuration data and commands to be passed on to selected communication devices of the second data transmission stage. Operating, status and medical data of all the attached communication devices of the second data transmission stage are likewise temporarily stored inside this third transmission stage, i.e. inside the server device.

The application operation units arranged in the fourth data transmission stage produce the configuration files and commands in an automated manner or with the aid of clinical staff. In addition, they make a selection of the communication units to be activated and define the functional and time-wise behaviour of the communication devices, by making available the data or information required for this in the server device according to the third data transmission stage.

The application operation units can also evaluate, concentrate and illustrate the operating, status and medical data, which are temporarily stored in the server device, in a suitable manner.

The application server unit is operated, controlled and regulated with respect to writing and reading data by the application operation units.

In the case of the method according to the invention, data which are received in at least one first memory unit and by means of a first control unit and which are transmitted by the medical appliances of the group, in particular appliance-specific and patient-specific data of patients who are connected up to the medical appliances, are stored temporarily and bundled in each communication device and are passed on to the memory server unit.

The data, in particular medicine-specific data, are likewise received and temporarily stored by the memory server unit or the application server unit by means of the first memory unit and the first control unit in order to send them on to selected medical appliances on demand or when required. This can occur for example when the medical appliance is in an operating state suitable for the updating with data. The communication device then carries out the transmission and the updating of the data in the medical appliance in an independent manner. To this end the data of all the medical appliances are continuously read out from the communication device and are temporarily stored inside the communication device.

As soon as these temporarily stored data, to which operating-status data of the medical appliances also belong, indicate that a suitable operating mode of the medical appliance is present, updating of a data bank of the medical appliance is carried out by the communication device. This must not take place in an operating state during which a current therapy by the medical appliance is being carried out.

It is preferable for the presence of new data, as well as also new configurations, to be indicated visually inside the medical appliance.

The first network is preferably of the CAN type and the second and third networks are of the WLAN and/or LAN type.

Further advantageous embodiments are set out in the sub-claims.

Advantages and expedient features are evident from the following description in conjunction with the drawing. In the drawing FIG. 1 is a diagrammatic illustration of the system according to the invention built up in a multiplicity of stages, and FIGS. 2a and 2b show a possible application of the multiple-stage system and method according to the invention in flow charts in the form of one embodiment.

Figure 2A:
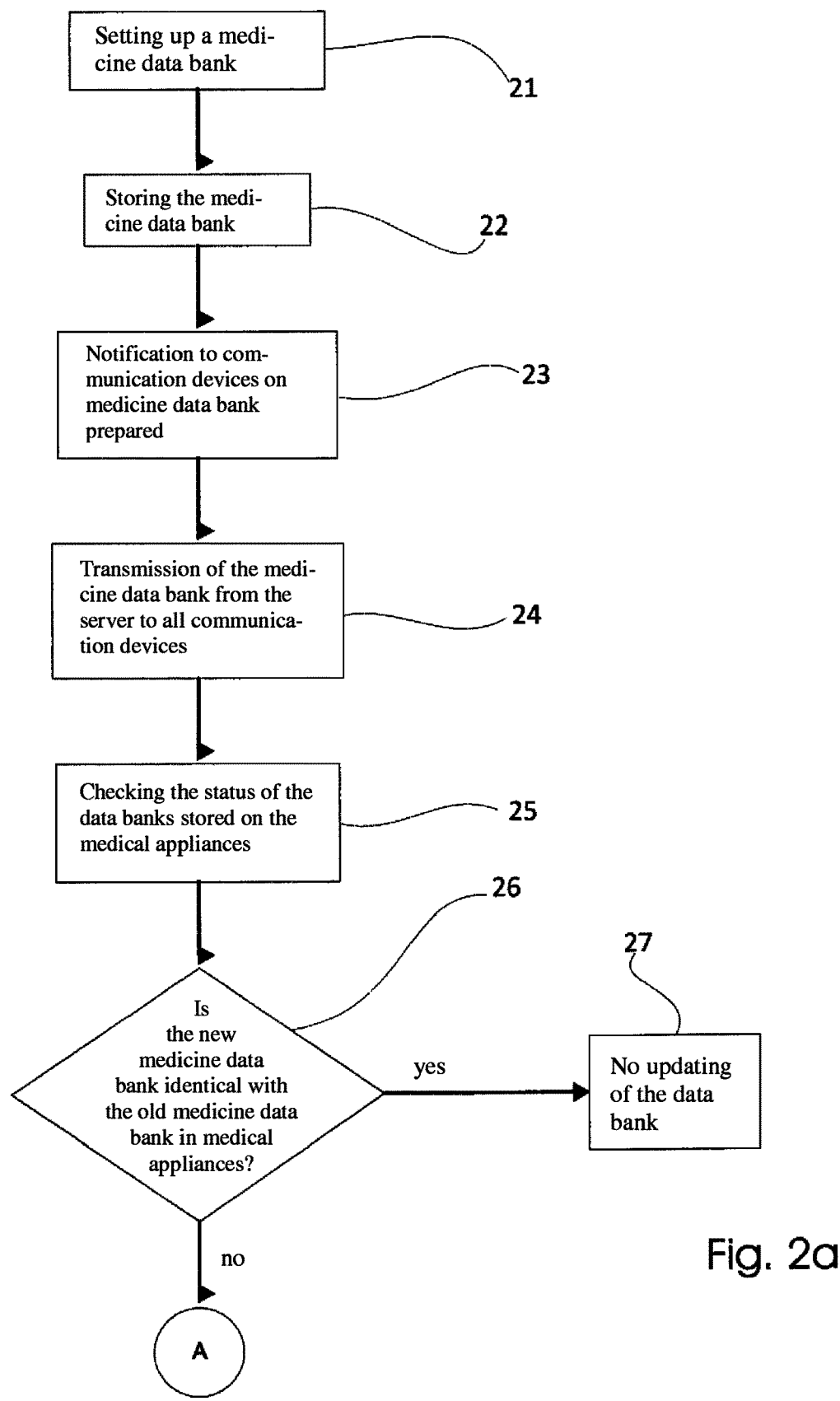
Figure 2B:
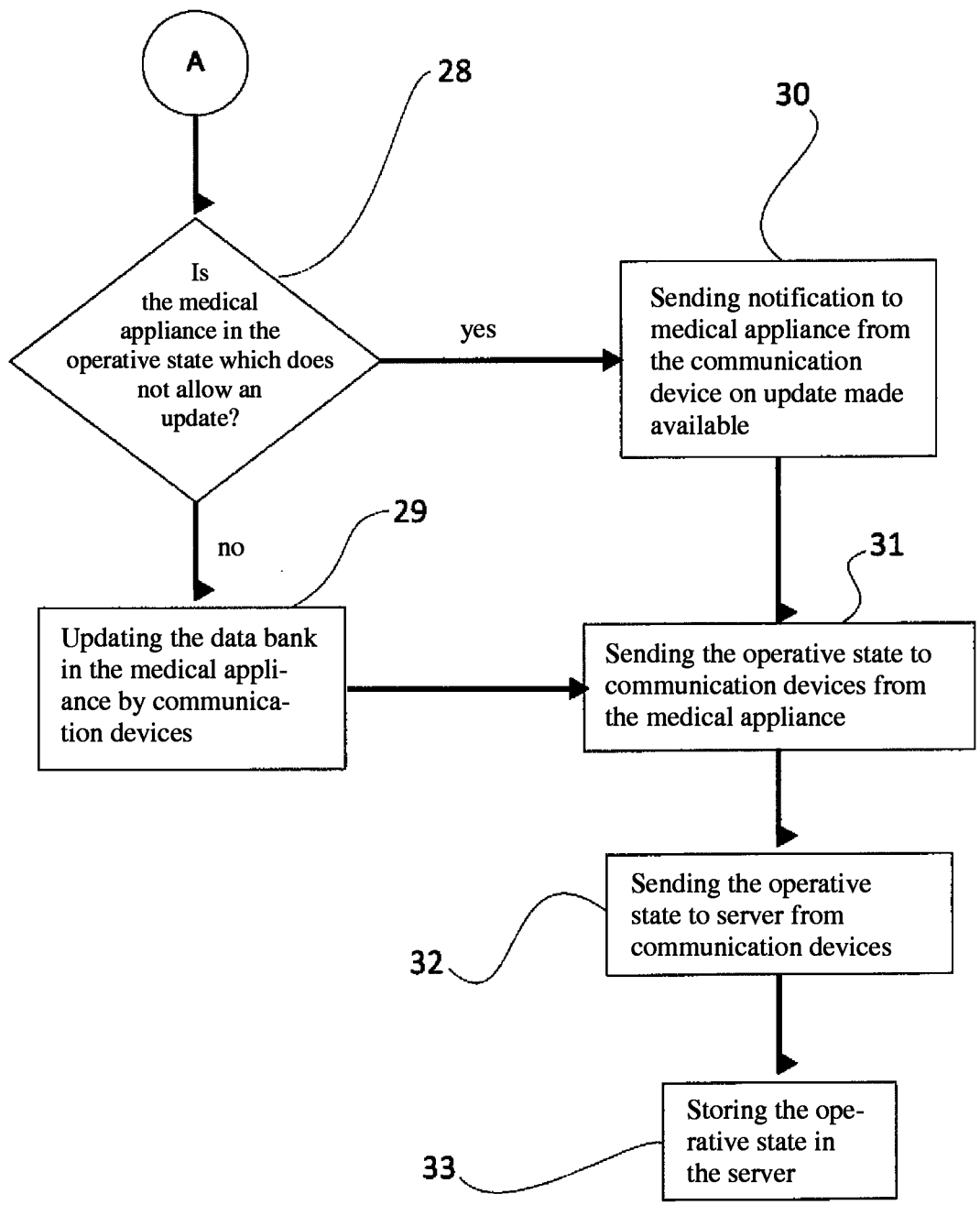

A diagrammatic illustration of the basic design of the system according to the invention for performing the method according to the invention for controlling the data transmission of a plurality of medical appliances is shown in FIG. 1.

This system permits the control and configuration of a plurality of medical appliances without failure of the transmission of data and without overloading the networks connected to them as well as the collection and visualization of further data which are sent by the medical appliances and are collected centrally for evaluation and monitoring purposes.

There are altogether four data transmission stages 1 to 4, a plurality of medical appliances 5, such as insulin pumps, being arranged subdivided into different groups 5a in the first data transmission stage 1.

One group 5a of medical appliances is assigned in each case to a communication device 6 with a first storage unit 6a and a first control unit 6b. This is carried out by means of an exclusive network based on CAN in accordance with the reference number 7. In this way, there is an exclusive CAN connection 7 between the communication device and each medical appliance assigned to it.

The plurality of communication devices 6 are connected in turn to a centrally arranged server device 8 by way of a second network 9, it being possible for the server device 8 to be subdivided into a memory server unit SS and an application server unit AS.

The server device 8 can in turn be connected by means of a third network 11 from the third data transmission stage 3 to the application operation units 10a, 10b, 10c which are arranged on the fourth data transmission stage 4 and which permit different applications A, B, C.

Such a multiple-stage design of the system according to the invention for promoting the transmission of data permits a trouble-free transmission of data which is not susceptible to overloading by way of the available networks.

An embodiment with a possible implementation of the method according to the invention, for which the system according to the invention is necessary, is illustrated in a flow chart in FIGS. 2a and 2b.

First of all, a new updated medicine data bank is set up by means of one of the application operation units. This is carried out in accordance with step 21.

After that, the medicine data bank is stored by the transmission of a corresponding control signal from the application operation unit to the server device 8 in accordance with step 22.

In accordance with step 23 all the communication devices 6 receive the notification that a new medicine data bank is available in the server device. After that, by demand or by sending the data for the new medicine data bank when required, a transmission of the medicine data banks takes place from the server to all the communication devices in accordance with step 24. This is carried out by way of the second network after the third network has been used in the transmission from the application operation units to the memory device.

The communication devices continuously receive data—from the medical appliances attached to them—on the current state or status of the respective medicine data bank, which are stored for the moment in the respective medical appliances.

As soon as this checking has been carried out in accordance with step 25, an enquiry is made—in a step 26 by sending an interrogation signal from the communication device to the respective medical appliance or by checking the current data which are present inside the communication device to the respective appliance—as to whether the data on the new medicine data bank are identical with the data on the previously present medicine data bank in the respective medical appliance. If this is the case, an updating of the medicine data bank does not take place in accordance with step 27.

If the data of the medicine data bank do not correspond, an enquiry is made in a further step 28 as to whether the medical appliance in question has assumed an operative state which allows an updating of the data bank or whether it is in a therapy method at the moment. If an operating state of the medical appliance is present which allows updating, then in accordance with step 29 an updating of the data bank of the medical appliance is carried out by the transmission of the data of the medicine data bank from the communication device of the medical appliance. After that, an actuation of the portion 31 is carried out, according to which the current operative state is sent from the medical appliance to the communication device.

If the operative state does not allow updating for the moment, in accordance with step 30 a notification on the update made available is sent from the communication device to the medical appliance. In response to this, in accordance with step 31, the medical appliance sends the current operative state to the communication device which in turn in accordance with step 32 sends it in the current operative state to the server which in accordance with step 33 stores the current operative state in order to update the central data bank on the operative states of all the appliances.

The communication device constantly checks the operative state of the medical appliances (step 28) and independently carries out an update as soon as the operative state of a medical appliance allows an update.

In accordance with arrow 34 a repeated enquiry as to the operative state by the communication device takes place until it is established that the operative state of the medical appliance in accordance with step 28 allows an updating of the medical appliance to be possible.

Consequently, during the transmission of operative and status information of the medical appliances to the server devices two stages of the transmission of data are followed, namely the transition from the first data transmission stage to the second data transmission stage and the transition from the second data transmission stage to the third data transmission stage.

On account of the first network—used exclusively by a medical appliance—with the communication device a current enquiry as to the operative state and a possibly occurring change of operative and status data of the individual medical appliance with a high degree of transmission quality and a low degree of failure is possible. These operative and status data are temporarily stored inside the communication device and prepared in order then to send them on in a bundled manner to the server device by means of the second network.

In this case the communication device records which data are sent when to the server device by means of the second network, and as a result it is capable of restricting the transmission of data to the server device to the recently arrived or received data.

If a failure of the second network were to occur, all the data for predefinable periods of time are temporarily stored inside the communication devices and they are transmitted completely to the server device when the second network becomes available again.

In accordance with a further embodiment of the invention it is possible for data also to be sent directly to other third systems from the communication device, without this having to take place by way of the server device. For this purpose, protocol adaptations can also be carried out inside the communication device.

On account of the reduction of the data—to be transmitted from each communication device 6 to the server device—to those data which have previously not yet been transmitted, it is possible to eliminate overloading of the second network 9. In the same way, the loss of data and latency times inside the first network 9 are eliminated as a result of the direct connection between each communication device 6 and each medical appliance 5, since each medical appliance 5 has stored in it its entire protocol and data. The storage of data inside the communication devices 6 for the case of power supply failures is no longer necessary as a result.

Certain features disclosed in the application are understood to be novel, including for example, features either individually or in combination with other features as compared with the prior art.

LIST OF REFERENCE NUMERALS

1, 2, 3, 4 data transmission stage
5, 5*a* medical appliances
6 communication device
6*a* memory unit
6*b* control unit
7 first network
8 central server device
9 second network
10*a*-10*c* application operation units
11 third network
21-34 method steps AS application server unit
SS memory unit

The invention claimed is:

1. A system for controlling a data transmission to and/or from a plurality of medical appliances, comprising:
   a plurality of appliance groups within a first data transmission stage, each of the plurality of appliance groups including at least one of the plurality of medical appliances;
   a plurality of communication devices within a second data transmission stage, each of the plurality of communication devices being connected to one of the plurality of groups by a first network, the second data transmission stage configured for the transmission, storage and control of data between the plurality of communication devices and the plurality of appliance groups; and
   a common central server device within a third data transmission stage, the central server device being connected to the plurality of communication devices by a second network, the third transmission stage being configured for the storage, control and transmission of data between the central server device and the plurality of communication devices;
   wherein each communication device is configured to:
      determine, with a processor, an operating state of each medical appliance in the one of the plurality of appliance groups connected to the communication device; and
      update a data bank associated with each medical appliance when the determined operating state indicates the medical appliance allows updating.

2. The system according to claim 1, wherein the second network directly connects the communication devices to the common central server device within the third data transmission stage.

3. The system according to claims 1, wherein the central server device comprises an application server unit and a memory server unit, wherein the application server unit is connected to application operation units on a fourth data transmission stage by a third network.

4. The system according to claim 3, wherein each of the plurality of communication devices has at least one first memory unit and one first control unit in order to store temporarily data arriving and received from the medical appliances of the group and to pass the data on in a bundled manner to the memory server unit.

5. The system according to claim 4, wherein the data comprise appliance-specific and patient-specific data on patients who are connected to the medical appliances.

6. The system according to claim 5, wherein the data comprise medicine-specific data.

7. The system according to claim 5, wherein the first memory unit and the first control unit of the communication device are suitable for storing temporarily data arriving and received from the memory server unit or the application server unit and to pass the data on to selected medical appliances upon demand or if required.

8. The system according to claim 3, wherein the third network connects the application operation units to the application server unit by means of a web interface and a web browser.

9. The system according to claim 1, wherein the medical appliances are insulin pumps.

10. The system according to claim 1, wherein each communication device is further configured to:
    receive status data from the data bank associated with each medical appliance;

compare the received status data is to current data stored in each communication device;
determine whether the received status data matches to the current data; and
transmit the current data to each medical appliance for updating the data bank of each medical appliance when the communication device determines the received status data does not match the current data stored in the communication device.

11. A method for controlling the transmission of data to and/or from a plurality of medical appliances, comprising:
subdividing the plurality of medical appliances into a plurality of appliance groups including at least one medical appliance in each group,
wherein each of the plurality of medical appliance groups on a first data transmission stage transmits data from or to one of a plurality of communication devices connected to one of the plurality of medical appliance groups and arranged on a second data transmission stage by way of a first network, each of the plurality of communication devices configured to control the one of the plurality of medical appliance groups to which the communication device is connected, and
wherein each of the plurality of communication devices transmit—by way of a second network—data from or to a common central server device arranged on a third data transmission stage, the common central server configured to control each of the plurality of communication devices;
determining, with one of the plurality of communication devices, whether the at least one medical appliance in the appliance group connected to the one of the plurality of communication devices is in an operative state that allows updating of a medical data bank of the at least one medical appliance; and
updating status data in the medical data bank of the at least one medical appliance when the one of the plurality of communication devices determines the at least one medical appliance is in an operative state that allows updating.

12. The method according to claim 11, wherein the central server device is provided with an application server unit and a memory server unit, wherein the application server unit is connected to application operation units on a fourth data transmission stage by way of a third network and is operated, controlled and regulated with respect to writing and reading data by the application operation units.

13. The method according to claim 12, wherein data which are received in at least one first memory unit and by means of a first control unit and which are transmitted by the at least one medical appliances of the plurality of medical appliance groups are stored temporarily in each communication device and are passed on in a bundled manner to the memory server unit.

14. The method according to claim 13, wherein the first memory unit and the first control unit of the communication device receive and temporarily store data, from the memory server unit or the application server unit in order to pass the data on to selected medical appliances upon demand or if required.

15. The method according to claim 11, wherein the first network is selected from the CAN type and the second and third networks are selected from the WLAN and/or LAN type.

16. The method according to claim 12, wherein the data comprise appliance-specific and patient-specific data of patients who are connected to the medical appliances.

17. The method according to claim 16, wherein the data comprise medicine-specific data.

18. The method according to claim 11, further comprising the steps of:
receiving, at one of the plurality of communication devices, status data from the data bank of the at least one medical appliance in the appliance group connected to the one of the plurality of communication devices; and
determining, with the one of the plurality of communication devices, whether the received status data matches current data stored in the one of the plurality of communication devices;
wherein the updating step is performed when the one of the plurality of communication devices determines that the received status data does not match the current data stored in the one of the plurality of communication devices.

* * * * *

UNITED STATES PATENT AND TRADEMARK OFFICE
CERTIFICATE OF CORRECTION

PATENT NO. : 10,026,504 B2
APPLICATION NO. : 13/574206
DATED : July 17, 2018
INVENTOR(S) : Horst Schmoll et al.

Page 1 of 1

It is certified that error appears in the above-identified patent and that said Letters Patent is hereby corrected as shown below:

In the Claims

Column 8, Line 52, should read:
7. The system according to claim 4, wherein the first Signed and Sealed this
Sixth Day of November, 2018

Andrei Iancu
*Director of the United States Patent and Trademark Office*